US008801698B2

(12) United States Patent
House

(10) Patent No.: US 8,801,698 B2
(45) Date of Patent: Aug. 12, 2014

(54) CATHETER RESERVOIR SEAL

(71) Applicant: Adapta Medical, Inc., Colorado Springs, CO (US)

(72) Inventor: Jamie Glen House, Colorado Springs, CO (US)

(73) Assignee: Adapta Medica, Inc., Colorado Springs, CO (US)

( * ) Notice: Subject to any disclaimer, the term of this patent is extended or adjusted under 35 U.S.C. 154(b) by 0 days.

(21) Appl. No.: 13/625,853

(22) Filed: Sep. 24, 2012

(65) Prior Publication Data
US 2013/0079756 A1    Mar. 28, 2013

Related U.S. Application Data

(60) Provisional application No. 61/538,620, filed on Sep. 23, 2011.

(51) Int. Cl.
*A61M 25/00* (2006.01)
*A61M 25/01* (2006.01)

(52) U.S. Cl.
CPC ....... *A61M 25/0017* (2013.01); *A61M 25/0111* (2013.01); *A61M 25/002* (2013.01); *A61M 25/01* (2013.01); *A61M 25/0113* (2013.01); *A61M 2025/0062* (2013.01); *A61M 2210/1085* (2013.01); *A61M 2210/1089* (2013.01)
USPC ........ 604/544; 604/540; 604/93.01; 604/317; 604/327

(58) Field of Classification Search
CPC .............. A61M 25/0111; A61M 25/0017; A61M 25/002; A61M 25/0097; A61M 25/01; A61M 25/0113; A61M 2025/0062; A61M 25/013; A61M 2210/1085; A61M 2210/1089; A61M 25/0068; A61M 2025/0046; B65D 39/06; B65D 51/002; A61J 2001/2041
USPC .......... 604/544, 19, 48, 93.01, 540, 317, 327, 604/328, 329; 215/355, 266, 312
See application file for complete search history.

(56) References Cited

U.S. PATENT DOCUMENTS

| 42,188 | A | * | 4/1864 | Hamilton | 215/266 |
| 2,367,883 | A | * | 1/1945 | Miller | 215/270 |
| 2,760,599 | A | * | 8/1956 | Sunden | 184/103.1 |
| 3,917,063 | A | * | 11/1975 | Chibret et al. | 206/221 |
| 5,380,315 | A | * | 1/1995 | Isono et al. | 604/416 |
| 5,409,141 | A | * | 4/1995 | Kikuchi et al. | 222/81 |

(Continued)

FOREIGN PATENT DOCUMENTS

JP    05278752 A  * 10/1993  ............. B65D 39/06

*Primary Examiner* — Adam Marcetich
(74) *Attorney, Agent, or Firm* — Moazzam & Associates, LLC

(57) ABSTRACT

A reservoir is incorporated in between a guide portion and an introducer tip of the introducer member. A spherical or similarly shaped plug is inserted into the guide portion. The plug is designed such that it forms a seal within the guide portion, preventing any fluid flow between the reservoir and an environment external to a distal end of the guide portion. This prevents a liquid or gel contained inside the reservoir from drying or leaking. The plug may further be held in place against a distal opening of the reservoir by positive pressure within the reservoir. The plug may further be held in place within the guide portion by a plurality of bumps or notches. When the catheter is advanced through the guide portion, the catheter tip pushes the plug into the reservoir, thereby breaking the seal and lubricating the catheter.

15 Claims, 3 Drawing Sheets

(56) References Cited

U.S. PATENT DOCUMENTS

| | | | |
|---|---|---|---|
| 5,423,793 A * | 6/1995 | Isono et al. | 604/410 |
| 6,164,501 A * | 12/2000 | Stradella | 222/386 |
| 6,255,101 B1 * | 7/2001 | Rousseau et al. | 435/288.1 |
| 6,578,709 B1 * | 6/2003 | Kavanagh et al. | 206/364 |
| 8,177,774 B2 * | 5/2012 | House | 604/544 |
| 2008/0097463 A1 * | 4/2008 | House | 606/108 |

* cited by examiner

CATHETER RESERVOIR SEAL

This U.S. Patent Application claims priority to U.S. Provisional Patent Application Ser. No. 61/538,620, filed Sep. 23, 2011, the content of which is hereby incorporated by reference herein in its entirety into this disclosure.

BACKGROUND OF THE SUBJECT DISCLOSURE

1. Field of the Subject Disclosure

The present subject disclosure relates to urinary catheters. More specifically, the present subject disclosure relates to the advancement of a catheter.

2. Background of the Subject Disclosure

Short term, or repeated catheterization of an individual's urinary bladder is a common practice today for many persons who are in a hospital setting, a nursing home, doctor's office, rehabilitation facility or at home. For instance, a user is sometimes catheterized to treat conditions such as urinary retention, the inability to evacuate urine, or for obtaining a sterile urine specimen from a user in a doctor's office.

The need for intermittent catheterization of an individual sometimes arises due to problems typically associated with long term use of indwelling catheters, such as infections, urethral damage, or bladder damage. Long term use of an indwelling catheter is also a risk factor for bladder cancer. This is often the case for persons having a neurogenic urinary condition, such as in a spinal cord injury, multiple sclerosis, stroke, trauma or other brain injury. Conditions that interfere with the individual's ability to voluntarily void the bladder may also arise post-surgically or as a result of benign prostatic hypertrophy or diabetes. Many of the affected individuals are capable of, and would prefer to perform self-catheterization. For many, the level of risk and discomfort of repeated catheterizations carried out over the course of a day (at 3-6 hour intervals, for example) are offset by the accompanying convenience, privacy or self-reliance that is achieved. Some of the major difficulties that arise in self-catheterization are the lack of satisfactory catheterization kits, the problem of maintaining the required level of sanitation during the procedure, and the difficulty of sometimes performing the procedure under conditions of restricted space and privacy.

In assisted, or non self-catheterizations, it is common practice in hospitals to employ a catheterization tray, which typically includes a sterile drape, gloves, a conventional catheter, antiseptic solution, swabs, lubricant, forceps, underpad and a urine collection container. Assisted catheterization is usually performed with the user in a supine position. Maintaining a sterile field during the procedure can still be a problem, however, and the "cath tray" procedure is impractical for use with some individuals and situations today.

Many individuals with spinal cord injuries or other neurological diseases routinely perform intermittent catheterization several times a day using conventional catheters or kits and "clean technique." Clean technique means that the urethral area is initially swabbed with antiseptic, and efforts are made to avoid contamination of the catheter during the procedure. The user's hands are not sterile and a sterile field is not maintained. Clean technique is used instead of sterile technique, generally, for two reasons. First, it is very difficult, if not impossible, for individuals who are performing self-catheterization to adhere strictly to sterile technique. Second, these individuals are required to catheterize themselves between 3 and 6 times a day, and the cost of a new sterile catheter and the accessories required to perform sterile catheterization become excessively expensive for many users. Sometimes an individual will reuse a "cleaned" catheter. As a result, the use of non-sterile technique will many times result in contamination and subsequent infection of the urinary tract, causing significant morbidity and cost to the user and society.

Even if cost was not a major consideration for the user, with most conventional self-contained sterile units where the collection bag doubles as the catheter insertion cover, the catheter is extremely difficult for the user to grasp and insert. This is particularly a problem for self-catheterization users who may also have neurological problems that limit manual dexterity. Also, with some of the available catheter kits and methods, the catheter is either not sufficiently lubricated during insertion (and thus requires the additional application of possibly non-sterile lubricant), or the catheter is too slick with lubricant and cannot effectively be grasped through an insufficiently flexible bag. As a practical matter, most individuals who would prefer to self-catheterize cannot conveniently do so, and maintain the required level of sanitation using many of the existing catheterization apparatus.

Many catheterization tasks require a degree of dexterity to accomplish. People with normal dexterity, like paraplegics, may not have use of their lower extremities, but their hands are normal. Quadriplegics can have use of their upper extremities, having absolutely normal movement, like a paraplegic, except for normal hand dexterity. Thus, many tasks requiring a degree of hand dexterity are very difficult for paraplegics to accomplish.

Spinal cord injuries at the C5, C6, or C7 level often affect the use of a person's hands and make these tasks difficult. However, people who have had strokes, brain injuries, or multiple sclerosis may also require catheterization but have limited dexterity. In this, and other ways, the current catheterization market does not currently support the needs of these people.

Insertion of a lubricated catheter is one such task. Current devices do not adequately prevent deterioration or loss of the lubricant before use.

SUMMARY OF THE SUBJECT DISCLOSURE

The present subject disclosure solves the problems described above by providing a sealed reservoir within an introducer member of a catheter assembly. In exemplary embodiments, the reservoir is incorporated in between a guide portion and an introducer tip of the introducer member. A spherical or similarly shaped plug is inserted into the guide portion. The plug is designed such that it forms a seal within the guide portion, preventing any fluid flow between the reservoir and an environment external to a distal end of the guide portion. This prevents a liquid or gel contained inside the reservoir from drying or leaking. The plug may further be held in place against a distal opening of the reservoir by positive pressure within the reservoir. The plug may further be held in place within the guide portion by a plurality of bumps or notches. When the catheter is advanced through the guide portion, the catheter tip pushes the plug into the reservoir, thereby breaking the seal and lubricating the catheter.

In one exemplary embodiment, the present subject disclosure is an introducer member for a urinary catheter assembly. The introducer member includes a proximal end being adapted for urethral insertion, a distal end for receiving a catheter, a throughbore extending from a first opening at said proximal end to a second opening at said distal end, a reservoir portion disposed within said throughbore, the reservoir portion including a lubricant, and a plug placed in between the reservoir portion and the second opening. The plug provides a seal between the reservoir portion and an environment external to the second opening.

In another exemplary embodiment, the present subject disclosure is a urinary catheter assembly. The assembly includes a catheter having a proximal end and a distal end, the proximal end being adapted for urethral insertion a guide portion to receive the catheter, a reservoir portion coupled to a proximal end of the guide portion, the reservoir portion including a lubricant, an introducer tip coupled to a proximal end of the reservoir portion, and a plug providing a seal between the reservoir portion and the guide portion.

In yet another exemplary embodiment, the present subject disclosure is an introducer member for a urinary catheter assembly. The introducer member includes a guide adapted to receive a catheter, a reservoir coupled to a proximal end of the guide, the reservoir including a lubricant, an introducer tip coupled to a proximal end of the reservoir, and a plug providing a seal between the reservoir and the guide.

DETAILED DESCRIPTION OF THE SUBJECT DISCLOSURE

The present application refers to subject matter described in commonly-owned U.S. Pat. No. 6,090,075, issued on Jul. 18, 2000, the contents of which are incorporated by reference herein in their entirety.

Example embodiments of the present subject disclosure include a catheter assembly including an introducer member. The introducer member includes a guide portion at a distal end of the introducer member, an introducer tip at a proximal end of the introducer member, and a reservoir incorporated in between the guide portion and the introducer tip, the reservoir including a lubricating liquid or gel. A proximal end is any portion of any part of the catheter assembly that is positioned closer to a urethra, and a distal end is any portion of any part of the catheter assembly that is positioned farther away from the urethra. A throughbore extends from an opening in the distal end of the guide portion through the entire introducer member, allowing a catheter to advance completely through the introducer member from the guide portion through the introducer tip. A plug is placed within the guide portion. The plug is designed such that it forms a seal at the opening of the guide portion, thereby preventing any fluid flow between the reservoir and an environment external to the distal end of the introducer member. This prevents the liquid or gel contained inside the reservoir from drying or leaking. The plug may be held in place against the distal opening of the reservoir by positive pressure within the reservoir. The plug may further be held in place within the guide portion by a plurality of bumps or notches. When the catheter is advanced through the guide portion, the catheter tip pushes the plug into the reservoir, thereby breaking the seal and lubricating the catheter.

The catheter may be enclosed in a sheath. The proximal end of the catheter may be positioned within a guide portion of an introducer member during manufacturing, and may remain there until use. Other elements such as collection bags, handles, etc. may be incorporated into the catheter assembly, and are described in U.S. Pat. No. 6,090,075.

Figure 1:
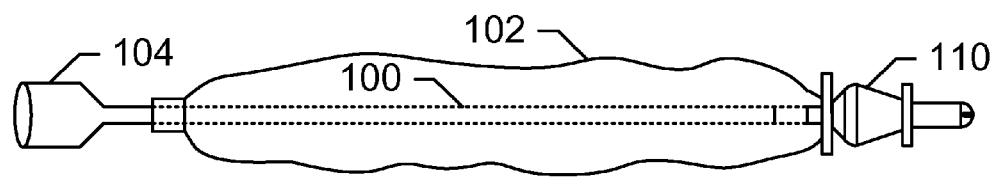
FIG. 1 shows a catheter assembly, according to an example embodiment of the present subject disclosure.

FIG. 1 shows a catheter assembly, according to an example embodiment of the present subject disclosure. In this example embodiment, the catheter assembly includes a catheter 100, a sheath 102, an outlet 104, and an introducer member 110. A substantial portion of the length of catheter 100 is surrounded by sheath 102, which acts as a protective envelope for catheter 100. The proximal end of catheter 100 slides through introducer member 110 located at the proximal end of sheath 102. Introducer member 110 is used to guide catheter 100 from within the sheath to a urethra via the throughbore. Catheter 100 is inserted into the distal end of introducer member 110 and proceeds through the throughbore to the proximal end of introducer member 110, emerging from an introducer tip of the introducer member and entering a urethra. Introducer member 110 is designed for urethral contact, and can be inserted into the urethra prior to catheter insertion. In this manner, the catheter is not exposed to the outside atmosphere prior to urethral insertion, in furtherance of a sterile insertion process free from any airborne microorganisms or particulates. The distal end of catheter 100 is coupled to outlet 104. Outlet 104 can be attached to a collection bag before use.

Introducer member 110 may be made of rigid or semi-rigid transparent or translucent plastic or silicon, or any other biocompatible, sterilizable and sufficiently inflexible material. Introducer member 110 must be able to retain its shape under the pressure of the insertion of catheter 100.

Figure 2A:
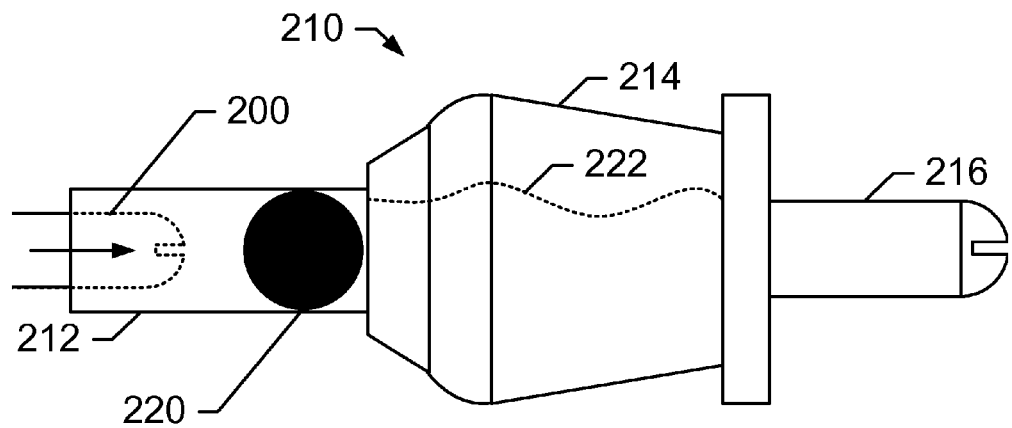
FIG. 2A shows an introducer member for a catheter assembly prior to insertion of a catheter, according to an example embodiment of the present subject disclosure.

FIG. 2A shows an introducer member 210 for a catheter assembly prior to insertion of a catheter 200, according to an example embodiment of the present subject disclosure. In this example embodiment, introducer member 210 includes a guide portion 212 including a plug 220, a reservoir portion 214 containing a lubricant 222, and an introducer tip 216. Plug 220 is placed within guide portion 212. Plug 220 is designed with dimensions such that plug 220 fits inside guide portion 212, yet seals the opening at the distal end of guide portion 212, thereby preventing any fluid exchange between reservoir portion 214 and an environment external to the distal end of guide portion 212. This prevents lubricant 222 contained inside the reservoir from drying or leaking. A proximal end (or tip) of a catheter 200 can be inserted through guide portion 212, pushing plug 220 into reservoir portion 214, thereby breaking the seal. Once plug 220 is pushed through, plug 220 will sit at the bottom or against a side wall of reservoir portion 214, and catheter 200 may advance past plug 220, through reservoir portion 214, into introducer tip 216, and eventually into the urethra.

Lubricant 222 may be a water-based lubricant, such as KY JELLY®, etc., or any other fluid suitable for lubricating catheter 200 for urethral insertion. For catheters made of a hydrophilic material or having a hydrophilic coating, lubricant 222 may simply be water or saline. Hydrophilic catheters are further described in commonly-owned U.S. Pat. No. 8,177, 774, issued on May 15, 2012, the contents of which are incorporated by reference herein in their entirety.

In this example embodiment, plug 220 is designed as a sphere. However, plug 220 may be of any shape sufficient to form a seal within guide portion 212, such as a cylinder, hemisphere, etc. Plug 220 may be made of rigid or semi-rigid transparent or translucent plastic or silicon, or any other biocompatible, sterilizable and sufficiently inflexible material, and can be the same material as introducer member 210. While the material must be sufficiently inflexible to maintain the seal, the material should be sufficiently flexible to allow a user to push plug 220 through guide portion 212 without substantial difficulty, especially for users having limited manual dexterity. The rigidity of the material can be balanced between maintaining the seal and allowing those having limited manual dexterity to push plug 220 through.

Figure 2B:
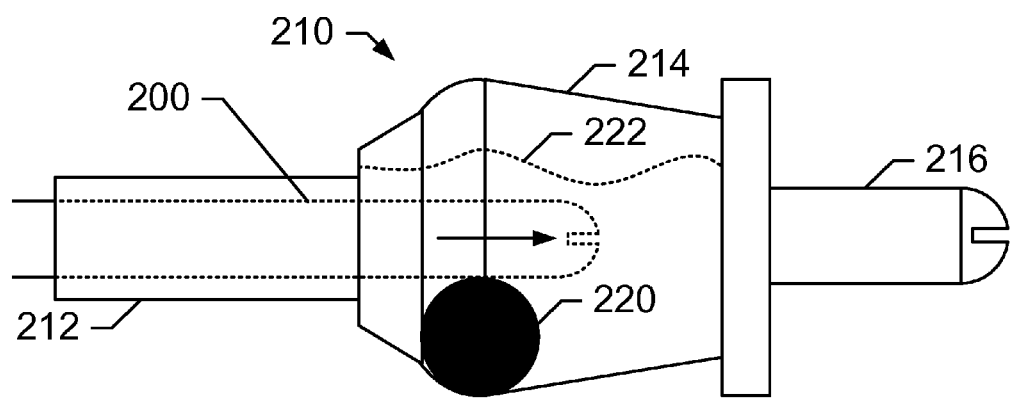
FIG. 2B shows an introducer member for a catheter assembly during insertion of the catheter, according to an example embodiment of the present subject disclosure.

FIG. 2B shows an introducer member 210 for a catheter assembly during insertion of catheter 200, according to an example embodiment of the present subject disclosure. In this example embodiment, introducer member 210 includes a guide portion 212, a plug 220, a reservoir portion 214 containing a lubricant 222, and an introducer tip 216. A catheter 200 has advanced into reservoir portion 214, pushing plug 220 into reservoir portion 214 in the process. With plug 220 resting within reservoir portion 214, catheter 200 can advance through reservoir portion 214 into introducer tip 216, from where it may be further advanced through a urethra. As catheter 200 advances through reservoir portion 214, lubricant 222 coats catheter 200 creating a lubricious surface on catheter 200, which aids urethral insertion.

Plug 220 may rest inside reservoir portion 214, and is sized such that it is unable to exit reservoir portion 214 into introducer tip 216. Since plug 220 is sized to fit within guide portion 212, the diameter of introducer tip 216 is sufficiently small so as to prevent plug 220 from entering introducer tip 216. Reservoir portion 214 is large enough so that plug 220 may rest inside while enabling catheter 200 to be advanced through reservoir portion 214.

The plug may further be held in place within the guide portion by a plurality of projections, such as bumps, notches, etc. As the catheter is pushed through the throughbore of the guide portion, it pushes the plug past the plurality of projections holding it in place, and into the reservoir, thereby breaking the seal. Similar to the plug, the bumps or notches may be of a material rigid enough to hold the plug in place, yet flexible enough to enable the plug to be pushed through by a catheter tip being advanced by a person having limited dexterity.

Figure 3A:
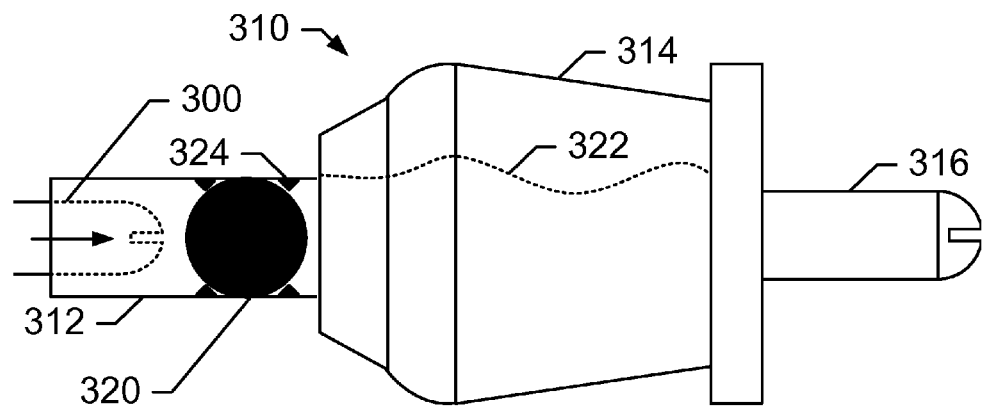
FIG. 3A shows an introducer member including projections prior to insertion of a catheter, according to an example embodiment of the present subject disclosure.

FIG. 3A shows an introducer member 310 including projections 324 prior to insertion of a catheter, according to an example embodiment of the present subject disclosure. In this example embodiment, introducer member 310 includes a guide portion 312 including projections 324 located on an inner surface of guide portion 312 for holding in place a plug 320. Introducer member 310 further includes a reservoir portion 314 containing a lubricant 322, and an introducer tip 316. Plug 320 is placed within guide portion 312 such that plug 320 is held in place by projections 324. Plug 320 is sized and designed such that plug 320 fits inside an opening of guide portion 312, yet plug 320 and projections 324 form a seal within guide portion 312, thereby preventing any fluid exchange between reservoir portion 314 and an environment external to the distal end of guide portion 312. Projections 324 are designed to hold plug 220 in place while enabling a user having limited manual dexterity to push plug 320 into reservoir 314 using a catheter 300.

Plug 320 may be designed to complement projections 324, and vice-versa, such that it is the combination of plug 320 and projections 324 that creates the seal. Plug 320 may also be designed to create the seal alone, and projections 324 simply hold plug 320 in place. The size and number of projections 324 may vary with the amount of force required to hold plug 320 in place. Projections 324 may hold plug 320 in place by blocking plug 320 from moving, by using friction, etc. For instance, projections 324 may be small and numerous, thereby converting an inner surface of guide portion 312 into a rough surface. Projections 324 may be made of rigid or semi-rigid transparent or translucent plastic or silicon, or any other biocompatible, sterilizable and sufficiently inflexible material, and can be the same material as introducer member 310.

Figure 3B:
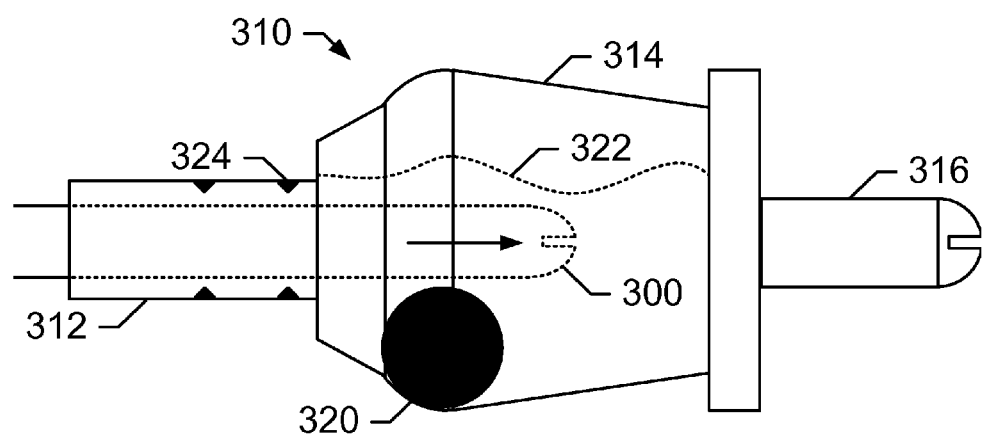
FIG. 3B shows an introducer member including projections during insertion of the catheter, according to an example embodiment of the present subject disclosure.

FIG. 3B shows an introducer member 310 including projections 324 during insertion, according to an example embodiment of the present subject disclosure. In this example embodiment, introducer member 310 includes a guide portion 312 including projections 324, a plug 320, a reservoir portion 314 containing a lubricant 322, and an introducer tip 316. A catheter 300 has advanced into reservoir portion 314, pushing plug 320 past projections 324 and into reservoir portion 314 in the process. With plug 320 resting within reservoir portion 314, catheter 300 can advance through introducer 316 as well, where it may be further advanced through a urethra. As catheter 300 advances through reservoir portion 314, lubricant 322 coats catheter 300 creating a lubricious surface on catheter 300, which aids urethral insertion.

Plug 320 may rest inside of reservoir 314 without being able to exit into introducer tip 316. Since plug 320 is designed with respect to guide portion 312, the diameter of introducer tip 316 is designed to prevent plug 320 from entering. Reservoir portion 314 is designed large enough so that plug 320 may rest inside without preventing catheter 300 from proceeding through reservoir portion 314.

The plug may further be held in place against the distal opening of the reservoir by positive pressure within the reservoir. As the catheter is advanced through the guide portion, relatively greater positive pressure from the distal end provided by the catheter tip pushes the plug into the reservoir, thereby breaking the seal and lubricating the catheter tip. Further, projections 324 are sized such that they retain plug 320 within guide portion 312 until pushed by catheter 300, yet allowing catheter 300 to freely advance past guide portion 312.

Figure 4A:
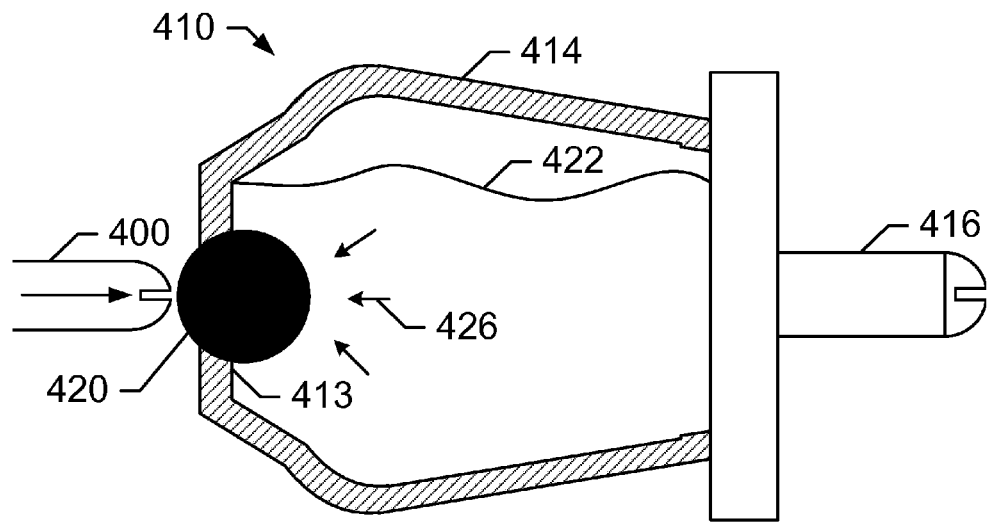
FIG. 4A shows an introducer member including a pressurized reservoir prior to insertion of a catheter, according to an example embodiment of the present subject disclosure.

FIG. 4A shows an introducer member 410 including a pressurized reservoir portion 414 prior to insertion of a catheter 400, according to an example embodiment of the present subject disclosure. In this example embodiment, introducer member 410 includes a reservoir portion 414 containing a lubricant 422 under a pressure greater than atmospheric pressure 426, an opening 413 in the distal end of reservoir portion 414, and an introducer tip 416. Plug 420 is placed against opening 413 of reservoir portion 414 and is held in place by positive pressure 426 inside reservoir portion 414. In this example embodiment, plug 420 is sized sufficiently large to fit within opening 413 without being able to exit past opening 413, while blocking lubricant 422 from exiting opening 413.

Plug 420 remains in place due to the positive pressure 426 within reservoir 414. As long as the pressure 426 is higher within reservoir portion 414 than outside of reservoir portion 414, plug 420 will remain in place separating lubricant 422 from opening 413. However, too much pressure within reservoir 414 may create difficulty in pushing plug 420 into reservoir 414 to break the seal. Therefore, the pressure 426 within reservoir 414 can be balanced between holding plug 420 in place and allowing users having limited manual dexterity to push plug 420 through.

The pressure 426 within reservoir 414 can be generated during manufacture and maintained until insertion of a catheter immediately prior to use. A penetrable membrane within introducer tip 416 can help seal the pressure 426 within reservoir 414. This membrane can be designed to seal when under pressure, and open when the pressure 426 is released. In this manner, once the pressure 426 is released from catheter 400 pushing plug 420 into reservoir 414, the membrane opens, allowing catheter 400 to advance through introducer tip 416. Other means for generating and holding pressure 426 within reservoir 414 will become readily recognizable to those having skill in the art upon reading this disclosure.

Figure 4B:
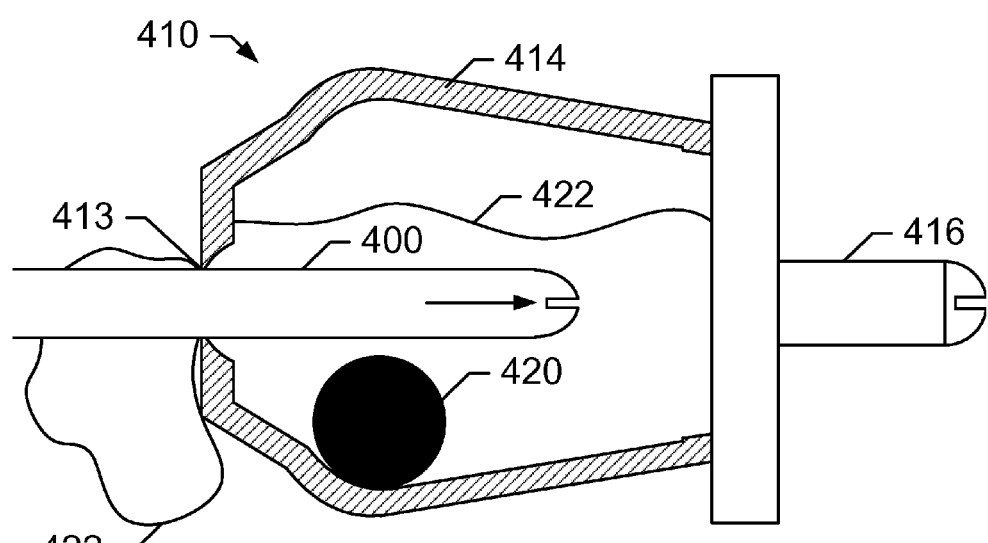
FIG. 4B shows an introducer member including a pressurized reservoir during insertion of the catheter, according to an example embodiment of the present subject disclosure.

FIG. 4B shows an introducer member 410 including a pressurized reservoir portion 414 during insertion of catheter 400, according to an example embodiment of the present subject disclosure. In this example embodiment, introducer member 410 includes an opening 413, reservoir portion 414 containing a lubricant 422 and including a plug 420, and an introducer tip 416. A catheter 400 has been advanced into reservoir portion 414, pushing plug 420 into reservoir portion 414, and releasing the positive pressure within reservoir 414 in the process. Lubricant 422 may leak out of reservoir 414 and into a cavity between catheter 400 and a sheath (not shown) covering catheter 400, especially when using water or saline as lubricant 422. This can help lubricate portions of catheter 400 prior to entering reservoir 414. With plug 420 resting within reservoir portion 414, catheter 400 can be advanced through introducer 416 as well, where it may be further advanced through a urethra. As catheter 400 advances through reservoir portion 414, lubricant 422 coats catheter 400 creating a lubricious surface on catheter 400, which aids urethral insertion.

Plug 420 may rest inside of reservoir 414, but should not be allowed to exit into introducer tip 416. Since plug 420 is designed with respect to opening 413, the diameter of introducer tip 416 is designed to prevent plug 420 from entering introducer tip 416. Reservoir portion 414 is designed large enough so that plug 420 may rest inside while still allowing catheter 400 to be advanced through reservoir portion 414.

Other means for sealing the distal end of the reservoir with a plug will become apparent to those having ordinary skill in the art in light of this disclosure. Further, adjustments can be made to prevent the plug from entering the throughbore at the proximal end of the reservoir and blocking the catheter from entering the introducer tip. For instance, a diameter of the throughbore in the guide portion may be sized larger than a diameter of the throughbore in the introducer tip, with the plug being sized to seal the throughbore in the guide portion. In this way, the plug is unable to inadvertently be pushed into the introducer tip. Further, the plug and catheter tip are designed such that the plug is unable to rest on the catheter tip and block the catheter from entering the introducer tip. The plug may further be of a material denser than lubricant 422, so that it sinks to the bottom of the lubricating reservoir, therefore not blocking the catheter from being advanced.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. An introducer member for a urinary catheter assembly, the introducer member comprising:
    a plug placed in between the reservoir portion and the second opening, the plug providing a seal between the reservoir portion and an environment external to the second opening;
    wherein the plug is held in place by positive pressure inside of the reservoir; and
    the introducer further comprises a penetrable membrane within an introducer tip that maintains the positive pressure inside the reservoir.

2. The introducer member of claim 1, wherein the plug is adapted to move into the reservoir portion when pushed by the catheter during catheter advancement.

3. The introducer member of claim 1, wherein the plug provides an airtight seal within the throughbore between the reservoir portion and the second opening.

4. The introducer member of claim 3, wherein the plug is held in place by a plurality of projections extending inward from an inner wall of the throughbore between the reservoir portion and the second opening.

5. The introducer member of claim 4, wherein the plurality of projections assist the plug with the seal.

6. The introducer member of claim 1, wherein the plug is larger than the second diameter of the throughbore.

7. A urinary catheter assembly, comprising:
    wherein a first throughbore of the guide portion has a greater diameter than a second throughbore of the introducer tip;
    wherein the plug is held in place by positive pressure inside of the reservoir; and
    the introducer further comprises a penetrable membrane within the introducer tip that maintains the positive pressure inside the reservoir.

8. The catheter assembly of claim 7, wherein the plug is adapted to move into the reservoir portion when pushed by the catheter during catheter advancement.

9. The catheter assembly of claim 7, wherein the plug is held in place by positive pressure inside the reservoir portion.

10. The catheter assembly of claim 7, wherein the plug is held in place by a plurality of projections extending inward from an inner wall of the guide portion.

11. The catheter assembly of claim 7, wherein the plug is larger than the second throughbore.

12. The catheter assembly of claim 7, further comprising a sheath substantially surrounding the catheter, wherein a proximal end of the sheath is coupled to the distal end of the guide portion.

13. An introducer member for a urinary catheter assembly, the introducer member comprising:
wherein a first throughbore of the guide has a greater diameter than a second throughbore of the introducer tip;
wherein the plug is held in place by positive pressure inside of the reservoir; and
the introducer further comprises a penetrable membrane within the introducer tip that maintains the positive pressure inside the reservoir.

14. The introducer member of claim 13, wherein the plug provides an airtight seal within the guide.

15. The introducer member of claim 13, wherein the plug is held in place by a projection extending from an inner wall of the guide.

* * * * *